United States Patent [19]
King et al.

[11] Patent Number: 5,812,272
[45] Date of Patent: Sep. 22, 1998

[54] APPARATUS AND METHOD WITH TILED LIGHT SOURCE ARRAY FOR INTEGRATED ASSAY SENSING

[75] Inventors: David A. King, Palo Alto; Nicholas Sampas, San Jose; Carol T. Schembri, San Mateo, all of Calif.

[73] Assignee: Hewlett-Packard Company, Palo Alto, Calif.

[21] Appl. No.: 790,837

[22] Filed: Jan. 30, 1997

[51] Int. Cl.$^6$ .......................... G01N 21/55; G01N 21/47; G01N 21/64; G01N 21/63

[52] U.S. Cl. .......................... 356/445; 356/432; 356/352; 356/360; 356/362; 422/82.05; 422/82.08; 436/518

[58] Field of Search ..................... 356/445, 432, 356/352, 360, 362; 422/82.05, 82.08; 436/518

[56] References Cited

U.S. PATENT DOCUMENTS

| | | | |
|---|---|---|---|
| 5,143,854 | 9/1992 | Pirrung et al. | 436/518 |
| 5,265,792 | 11/1993 | Harrah et al. | 228/6.2 |
| 5,429,807 | 7/1995 | Matson et al. | 422/131 |
| 5,472,672 | 12/1995 | Brennan | 422/131 |
| 5,474,796 | 12/1995 | Brennan | 427/2.13 |
| 5,510,270 | 4/1996 | Fodor et al. | 436/518 |
| 5,552,270 | 9/1996 | Khrapko et al. | 435/6 |

FOREIGN PATENT DOCUMENTS

| | | |
|---|---|---|
| 0268237 A2 | 5/1988 | European Pat. Off. . |
| WO89/10977 | 11/1989 | WIPO . |
| WO91/07087 | 5/1991 | WIPO . |
| WO92/10587 | 6/1992 | WIPO . |
| WO92/10588 | 6/1992 | WIPO . |

OTHER PUBLICATIONS

Fafard et al., "Red Emitting Semiconductor Quantum Dot Lasers", *Science,* vol. 274, Nov. 22, 1996, pp. 1350–1353.

Southern et al., "Arrays of Complementary Oligonucleotides for Analysing the Hybridisation Behaviour of Nucleic Acids", *Nucleic Acids Research,* vol. 22, No. 8, 1994, pp. 1368–1373.

Bare et al., "A Simple Surface–Emitting LED Array . . . ", *IEEE Photonics Technology Letters,* vol. 5, No. 2 (Feb. 1993). pp. 172–175.

Fodor et al., "Light–Directed, Spatially Addressable Parrallel Chemical Synthesis", *Science* vol. 251, 1991, pp. 767–773.

Gariepy, G. B., "Wafer Dicing: Theory and Practice", *Microelectronic Manufacturing And Testing,* Dec. 1985, Lake Publishing Corporation, Libertyville, IL.

Frank et al., "A New General Approach for the Simultaneous Chemical Synthesis of Large Numbers of Oligonucleotides: Segmental Solid Supports", *Nucleic Acids Research,* vol. 11, No. 13, 1983, pp. 4365–4377.

Salch et al., "Fundamentals of Photonics", *Semiconductor Photon Sources,* p. 638.

*Primary Examiner*—Susan A. Loring
*Attorney, Agent, or Firm*—Philip S. Yip

[57] ABSTRACT

A technique for analyzing target chemicals is provided. The apparatus of the technique contains an array of two or more light sources. Each of the array elements includes a light source. The light source has an emitting surface from which light can be emitted. Two or more binder chemical moieties are associated with the light sources at the emitting surfaces. These binder chemical moieties can bind target chemicals such that different target chemicals can be bound to the array. Light emitted by the light sources impinges on target chemicals bound to the light sources and will cause light interaction (e.g., fluorescence) with the target chemicals to result in a light pattern or patterns to indicate the presence or quantity of the target chemicals. The array is formed by a tiling technique involving the arrangement of tiles of array elements in a desired pattern.

20 Claims, 5 Drawing Sheets

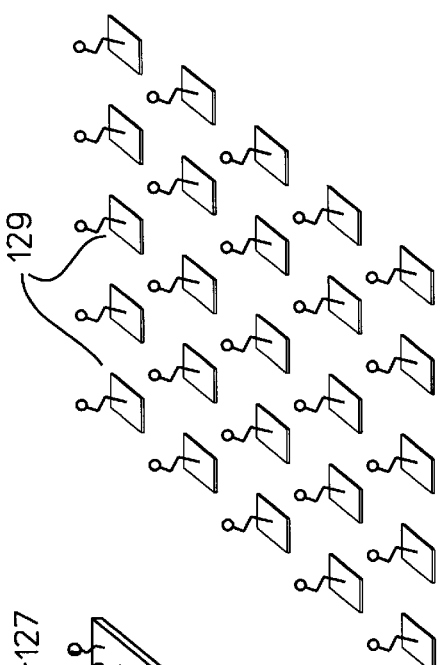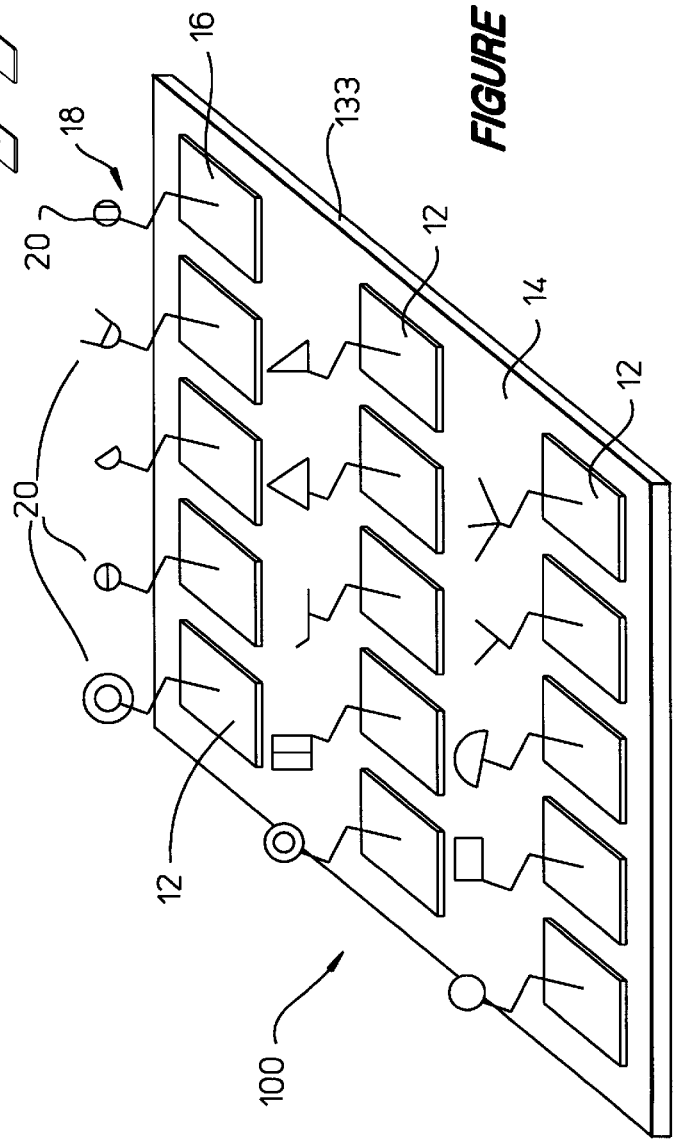

APPARATUS AND METHOD WITH TILED LIGHT SOURCE ARRAY FOR INTEGRATED ASSAY SENSING

FIELD OF THE INVENTION

The present invention relates to detecting chemicals in a chemical array and, more particularly, to providing a light source for detecting chemicals in a chemical array.

BACKGROUND

Recently, biomolecular arrays have been successfully created. For example, Fodor, et al., "Light-directed, Spatially Addressable Parallel Chemical Synthesis," *Science*, Vol. 251, 767–773 (1991) disclose high density arrays formed by light-directed synthesis. The array was used for antibody recognition. Biomolecular arrays are also described by E. Southern (PCT Publication WO 89/10977) for analyzing polynucleotide sequences. Such biomolecular arrays lend themselves to a large number of applications, from DNA and protein sequencing to DNA fingerprinting and disease diagnosis.

One approach for synthesizing a polymer array on an optical substrate is described by Fodor et al. (1991) supra; PCT publications WO 91/07087, WO 92/10587, and WO 92/10588; and U.S. Pat. No. 5,143,854. Because the apparatus and method of synthesizing a polymer array can be applied in the present invention, these disclosures are incorporated by reference herein. In this approach, an array of different receptors is synthesized onto a substrate using photolithographic techniques. Ligands are washed over the array. Either the ligand is fluorescently labeled or an additional fluorescently labeled receptor is also washed over the array. The result is that fluorophores are immobilized on those pixels where binding has occurred between the ligand and the receptor(s). The array is illuminated with radiation that excites the fluorophores. The pattern of bright and dark pixels is recorded. Information about the ligand is obtained by comparing this bright-dark pattern with known patterns of surface bound receptors. The aforementioned references describe a method for reading the array for the presence of fluorophores. For example, PCT publication WO 92/10587 discloses optically scanning an array by directing excitation with light through a microscope objective and collecting fluorescence through the same objective. Schembri et al. (Application Ser. No. 08/739,396, HP Docket No. 10960825-1) describe a chemical array formed by a tiling technique involving forming multiple tiles and picking and placing tiles on a support. However, techniques for forming arrays similar to those mentioned above requires relatively bulky optics for illuminating the chemical array.

King et al. (Application Ser. No. 08/520,456, HP Docket No. 1093347-1) describe an evanescent technique for illumining a large chemical array. They mentioned a few different light sources, including diode laser, vertical cavity surface emitting laser (VCSEL), and light emitting diode (LED). With such evanescent techniques, a complex chemical array needs to be formed in a complicated, in situ manner using synthesizing steps such as those used by Fodor et al. What is needed is an apparatus capable of illumining a chemical array with a compact light source that can be formed with a relatively straight forward process.

SUMMARY

The present invention provides an apparatus for analyzing target chemicals. The apparatus contains an array of two or more light sources (e.g., diode lasers) each having an emitting surface from which light can be emitted from the light source. Two or more binder chemical moieties are associated with the light sources at the emitting surfaces. These binder chemical moieties are for binding target moieties such that different target chemicals can be bound to the array. When activated, the light sources will emit light to cause light interaction (e.g., fluorescence) with the target chemicals to result in a light pattern or patterns to indicate the presence or quantity of the target chemicals.

The array elements each has a light source and one or more binder chemical moieties. The array elements are formed by a tiling technique. Generally, wafers of solid-state light-source material are coated with chemical with the desired binder chemical moieties suitable for binding the desired target chemicals, subdivided into smaller tiles, and the tiles are picked and arranged in a predetermined fashion. Such an array can be advantageously employed to analyze a sample suspected to contain certain analytes. By exposing the sample to the array, if a target chemical is bound to a particular location, its identity can be determined. By illumining the target chemicals bound to the array and detecting the resulting light interaction, the presence or quantity of the target chemicals can be determined.

The technique for constructing the array is relatively simple. Since each wafer can be made to target only one kind of target chemical, no complicated chemical synthesizing steps are necessary to form a complex arrangement containing numerous kinds of binder chemical moieties on the array. Because the solid-state light sources can be relatively small, by forming the binder molecules, or binder chemicals (which include the binder chemical moieties) on the light sources, a compact apparatus suitable for detecting target chemicals can be constructed. Furthermore, when bound to the light sources, the target chemicals are integral with the light sources. This integral arrangement offers great advantages for analyzing samples. There is no need to collimate or channel excitation light from the light sources to the target chemicals using additional, complex imaging optics such as light pipes, lenses, prisms, mirrors, beam-steering mechanisms, and the like. This greatly reduces beam distortion, noise, and the effort for aligning the light sources with the chemical array. Further, as an integral unit, the light sources and the binder chemical moieties, and therefore, the target chemicals bound thereto, are not easily separated. In this way, greater reliability is achieved. Additionally, with the present technique, an array with high chemical fidelity can be made. The quality of each individual wafer can be examined prior to the picking and placing of tiles into the array arrangement. Inferior tiles can be discarded to ensure that all the array elements in an array meet specification.

BRIEF DESCRIPTION OF THE DRAWINGS

The following figures show the embodiments of the present invention to better illustrate the apparatus of the present invention. In these figures, like numerals represent like features in the several views and the drawings are not drawn to scale for the sake of clarity.

FIG. 1 shows a schematic representation of the process of forming an array according to the present invention, showing the stages a, b, c, d, e, and f during the formation process.

DETAILED DESCRIPTION OF THE INVENTION

Figure 2:
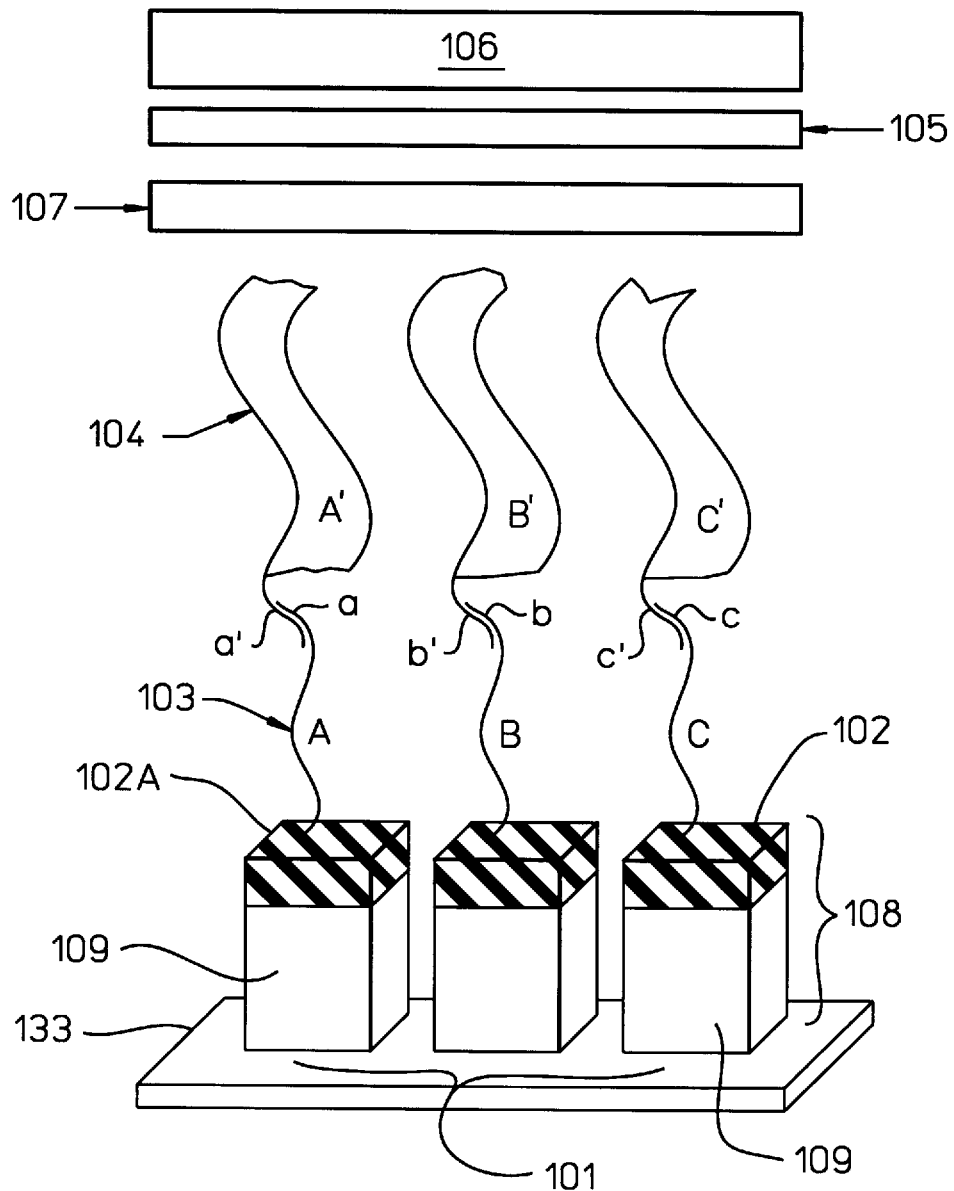
FIG. 2 shows a schematic representation of a portion of the apparatus according to the present invention, showing a portion of the array with detection optics.

The present invention provides an analyte-detection array with a plurality of light sources in integral relationship with binder chemical moieties for binding the analytes. The light sources are formed by subdividing wafers of light source material into smaller tiles.

In this specification and in the claims that follow, reference will be made to a number of terms, which are used as defined below.

An "array" is an arrangement of objects in space in which each object occupies a separate predetermined spatial position. Each of the objects in the array in an apparatus of this invention contains one or more species of binder chemical moiety attached to a light source, such that the physical location of each species is known or ascertainable.

A "wafer of light source material" is a unit of substantially planar material that can be handled and still maintain its identity. The wafer has a plurality of light sources arranged in a linear or two-dimensional fashion and can be subdivided into "tiles" which can be connected to an electrical source to emit light. The wafer can be derivatized to provide the binder chemical moieties. The tiles can be recombined in various ways to form a physical array. Preferably, the tiles will have regular geometric shapes, e.g., a sector of a circle, a rectangle, and the like, with radial or linear dimensions of about 100 $\mu$m to about 10 mm, most preferably about 250 $\mu$m to about 1000 $\mu$m. The subdivision of the light source material into tiles can be made either before or after attachment of the binder chemical moiety, and by any suitable method for cutting the wafer, e.g., with a dicing saw. These methods are well-known in the art of semiconductor chip manufacture and can be optimized by one skilled in the art for the particular material selected for use in this invention.

A "support" is a surface or structure for the attachment of tiles. The "support" may be of any desired shape and size and can be fabricated from a variety of materials. The support material can be treated for biocompatibility (i.e., to protect biological samples and probes from undesired structure or activity changes upon contact with the support surface) and to reduce non-specific binding of biological materials to the support. These procedures are w ell-known in the art (see, e.g., Schöneich et al, *Anal. Chem.* 65: 67–84R (1993)). The tiles can be attached to the support by means of an adhesive, by insertion into a pocket or channel formed in the support, or by any other means that will provide a stable and secure spatial arrangement. "Tiling" is the process of forming an array by picking and placing individual tiles containing single or multiple species of chemical moieties on a support in a fixed spatial pattern.

A "binder chemical moiety" is an organic or inorganic molecule, or a portion thereof, that can bind to a target chemical. In this invention, the binder chemical moiety is attached on a wafer of light source material prior to tiling, in distinction to an organic molecule that is synthesized in situ on an array surface, as done in prior art chemical array methods such as those used by Fodor, et al., supra. The preferred mode of attachment is by covalent bonding, although noncovalent means of attachment or immobilization might be appropriate depending on the particular type of chemical moiety that is used. If desired, a "binder chemical moiety" can be covalently modified by the addition or removal of groups after the moiety is attached to a wafer of light source material.

The binder chemical moieties of this invention are preferably "bioorganic molecules" of natural or synthetic origin, are capable of synthesis or replication by chemical, biochemical or molecular biological methods, and are capable of interacting with biological systems, e.g., cell receptors, immune system components, growth factors, components of the extracellular matrix, DNA and RNA, and the like. The preferred bioorganic molecules for use in the arrays of this invention are "molecular probes" selected from nucleic acids (or portions thereof), proteins (or portions thereof), polysaccharides (or portions thereof), and lipids (or portions thereof), for example, oligonucleotides, peptides, oligosaccharides or lipid groups that are capable of use in molecular recognition and affinity-based binding assays (e.g., antigen-antibody, receptor-ligand, nucleic acid-protein, nucleic acid-nucleic acid, and the like). An array may contain different families of bioorganic molecule, e.g., proteins and nucleic acids, but typically will contain two or more species of the same family of molecule, e.g., two or more sequences of oligonucleotide, two or more protein antigens, two or more chemically distinct small organic molecules, and the like. An array can be formed from two species of molecule, although it is preferred that the array contain several tens to thousands of species of molecule, preferably from about 50 to about 1000 species. Each species can also be present in multiple copies if desired.

An "analyte" is a molecule whose detection in a sample is desired and which selectively or specifically binds to a binder chemical moiety, such as a molecular probe. An analyte can be the same or different type of molecule as the molecular probe to which it binds.

A "target chemical" is a molecule that includes the analyte and can result in light interaction with excitation light emitted from the light source. The target chemical is capable of binding to the binder chemical moiety. The target chemical may also contain a label, which facilitates the light interaction. Examples of labels are fluorescent or phosphorescent materials. The analyte itself may be the target chemical if the analyte itself emits light, e.g., fluoresces, when it is illumined by the excitation light.

A "linker" is a molecule that is capable of linking the binder chemical moiety to the derivatized light source material. A linker may not be present if the binder chemical moiety is capable of binding to the derivatized light source material directly.

PREFERRED EMBODIMENTS

FIG. 1 shows an illustrative example of an array of the present invention. Stages (a), (b), (c), (d), (e), and (f) show the different stages for the fabrication of the array. (These stages will be described later.) The array 100 in FIG. 1(*f*) has a plurality of light sources 12 arranged on a surface 14 of a support 133. Each of the light sources has a surface 16 on which binder molecules 18 are attached. Each binder molecule 18 has a binder chemical moiety 20 suitable for binding a target moiety of a target chemical. A variety of binder chemical moieties 20 are present on the surfaces of the light sources 12 such that different target chemicals can be bound to the array 100. Preferably, each light source 12 has only one kind of binder chemical moiety associated with it such that each light source will associate with one kind of target chemical.

On each of the target chemicals is a light interaction moiety (e.g., a fluorophore) which will result in a light interaction (e.g., florescence) when the light interaction moiety is activated by light emitted from the light source with which it is associated. In this way, by activating the light sources 12, the presence or quantity of target chemicals bound to the binder chemical moiety on the light sources can be determined.

FIG. 2 shows an example of the analytical apparatus of the present invention for analyzing chemicals in a chemical arrays. On a support 133 is an array 101 of light sources 108 including solid-state light (or optical) source 109. Examples of solid-state light sources 109 suitable for application in the present invention include vertical cavity surface emitting laser (VCSEL), light emitting diode (LED), and diode laser. Preferably, each one of the light sources 108 are such solid-state light sources. In this embodiment, each of the solid-state light sources are made by tiling (or dicing) a large wafer of solid-stated light source material into smaller pieces. As a result of the tiling process, each of the tiles has a light emitting surface 102 that has straight edges 102A. However, if desired, the light sources can be cut to have nonstraight edges. Attached to the surfaces 102 of the light sources 108 are binder molecules 103. In FIG. 2, as an illustrative example, three types of binder molecules (A, B, C) are shown, each of which has its respective binder chemical moiety (a, b, c). The binder chemical moiety (a, b, c) can be used for binding to target moieties (a', b', c') which are associated with target chemicals (A', B', C'). In this way, by having a plurality of the light sources, e.g., 109, in the array 101, a variety of target chemicals 104 can be bound.

When electricity is applied to the light sources, e.g., solid-state light sources 109, in the array 101, the light sources emit light to impinge on the target chemicals. The target chemicals, each of which containing a label, will result in light interaction when excitation light from a light source is impinged on it. Examples of light interaction suitable for application in detecting target chemicals include fluorescence and phosphorescence, light scattering, and light absorption. The light as a result of the light interaction can be detected by a light detector 106.

In light interactions that result in light of a wavelength different from that of the excitation light, light as a result of the light interaction can be spectrally filtered to exclude the light sources' excitation radiation by filter 105. An example of a suitable filter is a dielectric coating filter. In light interaction that involves absorption, the detector will detect a decrease in light transmission. In detecting light interaction involving light scattering, the light detector should be positioned such that the direct path of excitation light does not pass through the detector. In this way, the excitation light will not produce false signals. Optionally, an optical collecting and imaging system 107, e.g., including lenses, may be used to collimate the light from the light interaction through the filter 105 to impinge on the detector 106, thereby enhancing the optical signals.

Figure 3:
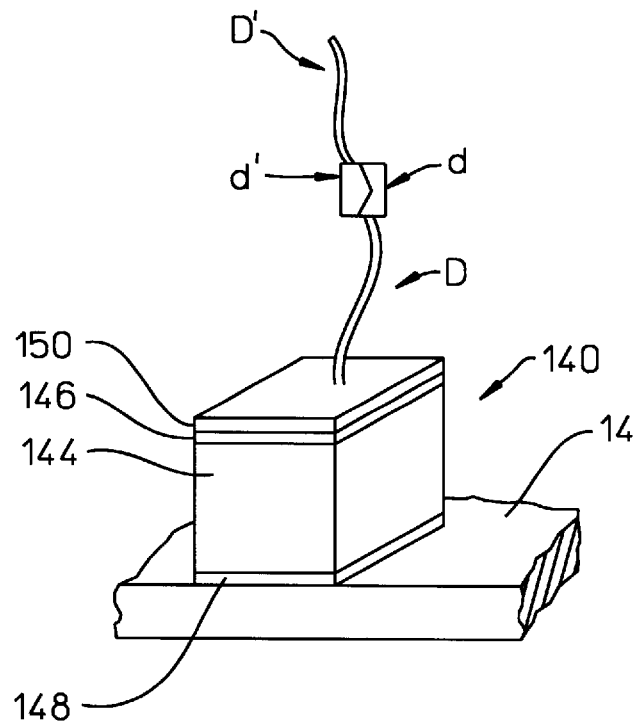
FIG. 3 shows a schematic representation of details of a portion of an array according to the present invention.

FIG. 3 shows further details of an embodiment of the present invention, in which the light source is a diode laser. Only a portion of the array is shown. The diode laser 140 is attached to a support surface 14. The diode laser 140 has a gain medium 144 sandwiched between a top reflector 146 and a bottom reflector 148. Each of the reflectors 146, 148 is preferably made of layers of dielectric material. Layered on top of reflector 146 is a coating 150 suitable for the attachment of a binder molecule D. The binder molecule D has a binder chemical moiety d suitable for binding to a target moiety d' of a target chemical D'.

Figure 4:
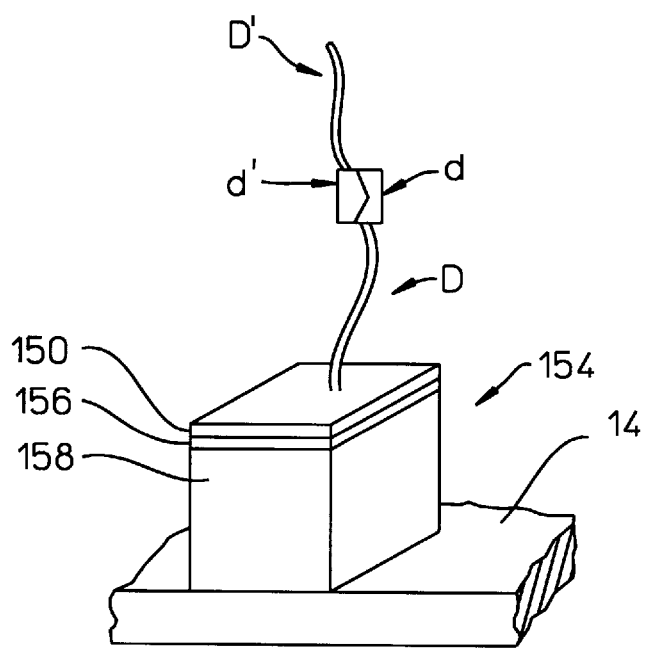
FIG. 4 shows a schematic representation of details of another embodiment of an array according to the present invention.

FIG. 4 shows a portion of yet another embodiment of the array of the present invention. In this embodiment, the light source is a light emitting diode (LED). The light emitting diode 154 has a layer of dielectric material 156 disposed on top of a layer of light emitting material 158. Again, on top of the LED 154 is a coating 150 suitable for the attachment of binder molecules, e.g., binder molecule D.

Figure 5:
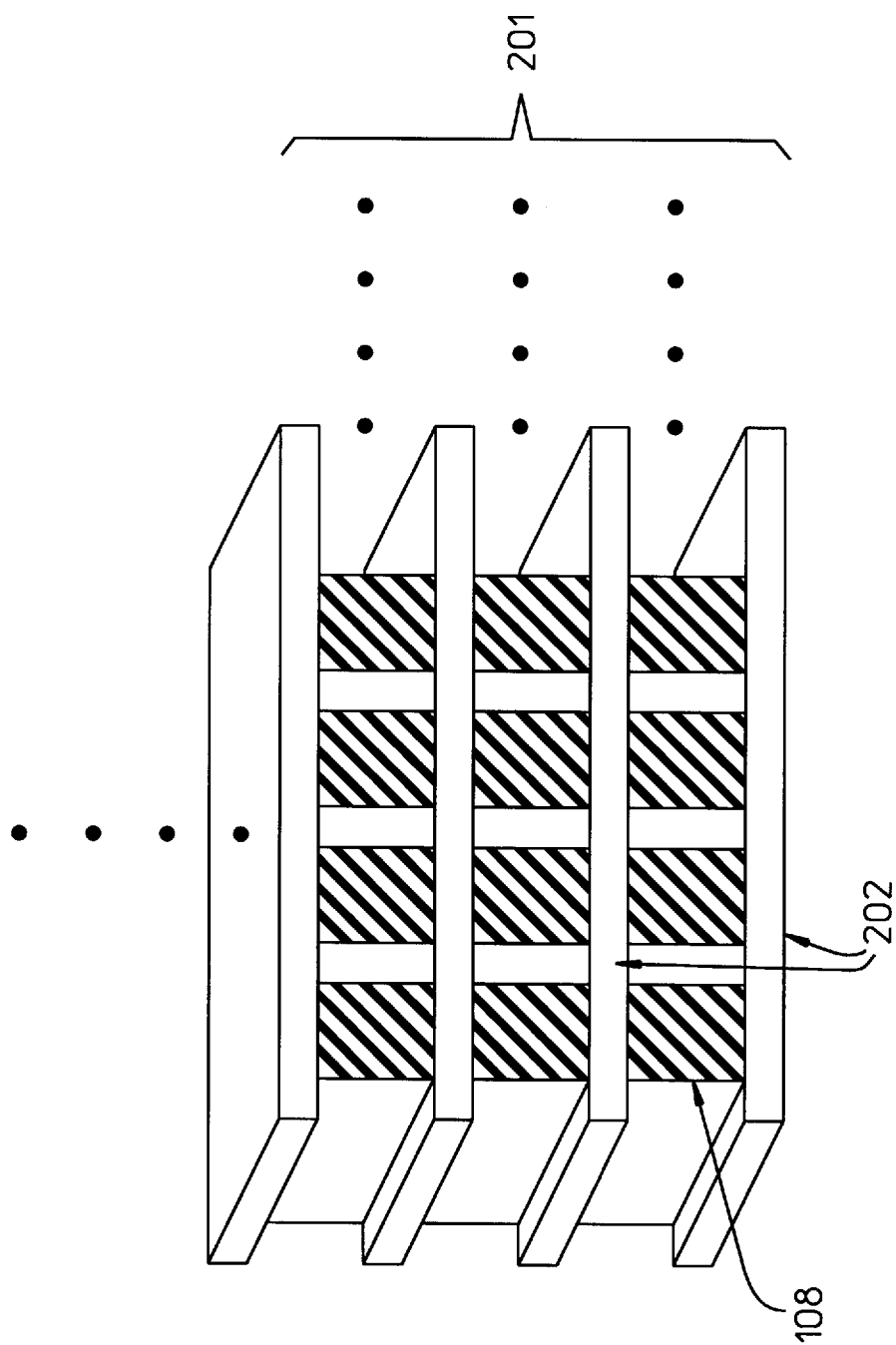
FIG. 5 shows a schematic representation of an embodiment of arrangement of array elements in an array in portion according to the present invention.
Figure 6:
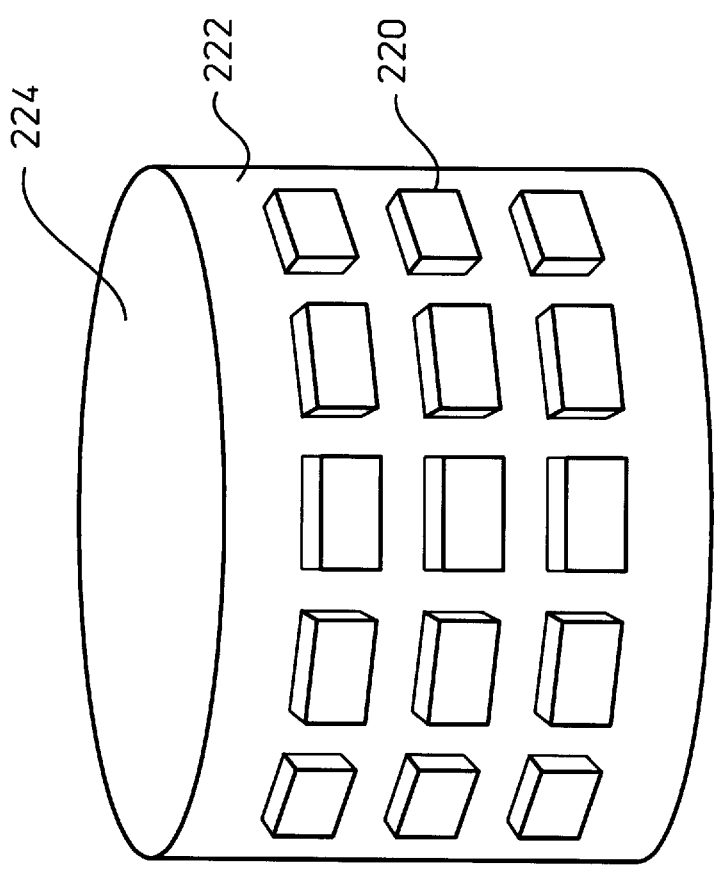
FIG. 6 shows a schematic representation of an embodiment of an array arranged in a circular fashion according to the present invention.

FIG. 5 shows an embodiment of the present invention in which the chemical array 201 is formed by stacking multiple linear arrays of light source units 108. Supports 202 include electrical contacts to activate the light source units 108. The dots showing in FIG. 5 indicate that additional light source units and additional layers of linear arrays can be added. There can be hundreds, even thousands of elements or more, in an array. The light sources in the array can also be arranged in a circular or cylindrical fashion as shown in FIG. 6. In this arrangement, the light sources 220 are arranged on the cylindrical surface 222 of a support 224.

Forming the array

FIG. 1 shows how a typical array is formed. A substantially planar wafer of solid-state light source material (step a, 121) is derivatized with chemically reactive groups (step b, 123). These groups are covalently attached to linker molecules (step c, 125). Of course, either or both of these steps can be bypassed if suitable functional groupings and/or linkers are inherent in the material selected for use. The linkers serve as attachment sites for binder chemical moieties. The linkers are contacted with a solution or droplets of binder chemical moieties. After binding has taken place between the linkers and binder chemical moieties, unreacted moieties are removed by washing with a suitable liquid, e.g., water. In this way, binder molecules are formed. Unreacted linkers are treated so as to render them chemically inert in successive array manufacturing steps and minimize their ability to interact with analytes during subsequent assay procedures. This treatment is generically referred to herein as "capping". Thus, e.g., a reactive aldehyde or isothiocyanate group can be capped with an amine or ammonia, a reactive epoxy group can be converted with an acidic solution into a diol, and so on. In step (d), all of the linkers are shown attached to the same species of binder chemical moiety (127). It should be understood, however, that more than one species of binder chemical moiety may be linked to a particular linker if so desired.

The wafer material is subdivided into individual tiles (step (e), 129). The subdivision can take place prior to or after step (b). In step (f), tiles containing the same or different species of binder chemical moiety (shown generally at 20) are arranged on a support (133) to form an array. In an embodiment of the invention shown in FIG. 6, the tiles (220) are cylindrically arranged on a surface (222) of a support (224). The support can be a solid rod having tiles disposed on the periphery as shown here, or the support can be a tubular structure wherein the tiles are disposed on the exterior or interior surface of the tube, or between exterior and interior surfaces, if these are spaced apart. Other variations of this shape are intended to be within the scope of this invention.

A variety of suitable light source material can be used, provided the material is capable of subdivision into tiles, compatible with the chemistry selected for attachment of binder molecules to the light-emitting surface with the suitable binder chemical moieties, and compatible optically with the detection method of the assay in which the array is to be used. Examples of suitable material include, without limitation, vertical cavity surface emitting laser (VCSEL), light emitting diode (LED), and diode laser, all of which have light-emitting facets (or surfaces). It is contemplated that quantum dot laser diodes can also be used. Examples of literature references to such light source material include, e.g., Salah and Teich, *Fundamentals of Photonics*, Wiley-Interscience, New York, 1991, pp. 593–641, and Bare et al., "A simple surface-emitting LED array useful for developing free-space optical interconnects," *I.E.E.E., Photon. Tech. Lett.*, Vol. 5, 172–175, 1993, and (regarding an array of vertical-cavity surface-emitting lasers (VCSEL)): Salah and Teich, supra, p. 638.

Based on the present disclosure, a person skilled in the art will know how to chemically derivatize and divide wafers of such solid-state light emitting source material into tiles. It is to be understood that on a wafer of VCSEL, the planar surface of the wafer is the light emitting surface and that this surface can be chemical derivatized and divided into tiles. In edge-emitting laser diodes, the emitting surfaces of laser diodes on a wafer are on the edge in the form of a linear array. In this case, the light emitting surface on this linear array (wafer) is chemically derivatized to impart the binder chemical moieties and then divided into tiles.

Various techniques can be used to attach linker or binder molecules to the light sources. One routine method for derivatizing a glass or silicon surface, and which can be used for derivatizing the light-emitting facets of the light sources, for attachment of binder or linker molecules, is by formation of siloxane bonds, using organosilanes such as 3-glycidoxypropyl- trimethoxysilane ("GOPS"), 3-aminopropyltriethoxysilane (APS), and the like, which have well-understood chemistries. The linker molecule may be a bifunctional reagent that covalently binds the surface to one group and the binder chemical moiety to the other. Alternatively, the linker may be a reagent that is bound to the surface covalently (e.g., streptavidin, avidin, etc.) and to the molecule of interest by a high affinity noncovalent interaction(e.g., biotin). Methods for covalently linking binder chemical moieties to various materials for use in affinity purification procedures are well-known. See, generally, *Affinity Techniques. Enzyme Purification: Part B. Methods in Enzymology*, Vol. 34, ed. W. B. Jakoby, M. Wilchek, Acad. Press, New York (1974) and *Immobilized Biochemicals and Affinity Chromatography, Advances in Experimental Medicine and Biology*, Vol. 42, ed. R. Dunlap, Plenum Press, New York (1974). The covalent attachment of oligonucleotides to solid supports for use in hybridization assays is described in Ghosh & Musso, *Nuc.Acids Res.*15: 5353–5372 (1987) and Eggers et al, *BioTechniques* 17: 516–524 (1994). Of course, the attached binder chemical moieties should be able to interact freely with target chemicals in binding assays (e.g., an attached oligonucleotide should be free to hybridize to a complementary nucleic acid or to bind a sequence-specific protein, an antigen must be capable of interacting with an antibody, and so on). Other examples of publications related to binding chemicals to a substrate include, Southern et al., PCT publication 89/10977; Barrett et al. PCT publications WO 91/07087, Pirrung et al. U.S. Pat. No. 5,143,854, and Fodor et al., WO 92/10092.

The binder chemical moieties intended for use in the arrays of this invention are generally bioorganic molecules as defined above, having molecular weights in the range of about several hundreds of daltons to about several hundreds of kilodaltons. Preferably, the density of molecules attached to a light source in a single tile is to be in the range of about 1000 to about 100,000 molecules per square micron of surface.

In light interaction, such as fluorescence and phosphorescence, when light from the light source impinges upon the label, the light resulting from the light interaction has a different, generally longer, wavelength than the excitation light emitted from the light source. Therefore, the excitation light poses less of a noise problem since a filter can be used to reduce its intensity such that the fluorescence or phosphorescence light can be selectively detected. Examples of suitable labels that can be used include well known and commonly available ones such as fluorescein, indocarbocyanine dyes (e.g., CY3, CY5), TEXAS RED, ethidium bromide, and chelated lanthanides. In some cases, to increase the light interaction signal, a receptor that is capable of binding to many molecules of a label can be bound to the analyte and included in the target chemical, which, of course, can be bound to the binder molecule on the light source. These techniques of labeling and measurements are within the knowledge of one skilled in the art. See, e.g., Barrett et al., PCT publication WO 91/07087.

In gathering signals in the light interaction, one way to reduce noise is to use labels compatible with time-resolved fluorescence, which is known to those skilled in the art of chemical analysis using labels. This is particularly beneficial in the frequency-multiplexing technique, which will be discussed later. The used of time-resolved fluorescence provides a phase difference between the excitation light and the fluorescence light, thereby enabling the background and noise to be reduced and suppressed. Time-resolved fluorescence preferentially requires wide bandwidth detectors and light sources. Typical dyes for time-resolved fluorescence suitable for the present invention have lifetimes on the order about tens of nanoseconds or less, e.g., ethidium bromide. Thus, light sources and light detectors with bandwidths greater than about 1 MHZ are preferred.

In light interaction in which no change in the spectral frequency is expected when the target chemical is illumined, e.g., light absorption or light scattering, no label may be needed and the analyte is the target chemical. However, a label may be used to facilitate the light absorption or light scattering.

To derivatize the light source material, the binder chemical moieties are contained in a solution that can be delivered to the attachment surface of the wafer in the form of droplets (see, e.g., EP 0268237 for an example of an apparatus suitable for dispensing and printing reagents) or, preferably, the solution can be held in contact with the surface. It is contemplated that some of the arrays formed by the process of this invention will contain multiple species of linker molecules or a single species of linker molecules.

As noted above, the tiles can be formed in any manner appropriate for subdividing the light source material. One method is by saw-dicing. Typically, the material is diced with a commercial dicing saw in the following manner. The material, e.g., wafer, is placed on a thin film adhesive backing for mounting on a vacuum chuck. The dicing instrument is programmed with information about the shape of the material to be cut, the desired depth of cutting, and speed of travel of the chuck towards the blade (assuming the position of the blade is fixed). The material is cut in a first direction with a blade, e.g., a metal or diamond-impregnated blade rotating at a speed of about 20,000 r.p.m. Debris generated by cutting can be directed away from the cut surface with a jet of air, gas or liquid. The material is then rotated through a desired angle and cutting is continued in a second direction until the formation of tiles is completed. An example of references on dicing solid-state wafers is Gerry Bariepy, "Wafer dicing: Theory and Practice," *Electronic Manufacturing and Testing*, December, 1985.

Another method of forming the tiles is by cleaving. Crystal lattices are found in a wafer of solid-state material. The wafer can be cleaved along lines in the crystal lattices, thereby allowing relatively clean separation of cleaved parts without forming much debris. Depending on whether the wafer is a wafer on the planar surface (such as VCSEL) or an edge-emitting light emitting water, (such as a slab of edge-emitting laser diode), slightly different division technique may be employed. Based on the present disclosure, those skilled in the art will be able to divide the wafer into tiles of light sources.

A tiled array of the present invention is formed by a tiling process involving transferring the tiles, obtained from wafers with a variety of linker molecules and binder chemical moieties, to a support in a stable predetermined spatial arrangement. The tiling or transfer (herein referred to as "picking and placing") can be performed with procedures that are known in the manufacture of integrated circuits and LEDs (see, e.g., U.S. Pat. No. 5,256,792). The following automated procedure is an example of a robotics procedure that has been used to pick and place tiles containing oligonucleotides and proteins, e.g., one at a time, on a support in a stable spatial arrangement. An individual tile in a group of tiles from a wafer within an x-y grid is located with the aid of a camera. The tile is picked up with a vacuum probe, re-inspected with a camera, moved with an x-y planar motor to a predetermined position on a support, and inserted into a holder in the support. The tiles can be arranged in a circular pattern and held in place by grooved channels formed within the support. Alternatively, the tiles can be held by an adhesive. Since we know the origin of each tile (i.e., the wafer from which the tile originated), we know the target chemicals that would be bound by each tile. The techniques for forming microstructures such as pockets, grooves, or channels capable of attaching tiles in a support are well-known in the art of microfabrication. Another alternative arrangement is that shown in FIG. 5. Wiring is provided to connect electrically the light sources to an electricity source and a control (switch) device that controls the activation of the light sources.

The arrays of the present invention are intended for use in a molecular recognition-based assay for the analysis of a sample suspected of containing one or more target chemicals (labeled analytes), whose detection is desired. The sample is brought into contact with an array of molecules of known structure or activity located at predetermined spatial positions on a support. Any fluidics system, or fluid-handling system, suitable for introducing a liquid sample to an array can be used for this purpose. For example, the fluidics system can contain tubings, bottles of reagents, pipettes, valves, electrical controls, and the like, known to those skilled in the art.

The target chemical, and therefore the analyte, is recognized by and selectively bound to an array light source; and the binding is of sufficiently high affinity to permit the analyte to be retained by the array light source until detection of the analyte has been accomplished. The selective recognition might be based on a distinguishing physicochemical characteristic of the analyte (e.g., a domain having a particular charge distribution or polarity that is capable of recognition by an array molecule), or a specific chemical feature of the analyte (e.g., a specific primary sequence in a nucleic acid, protein or polysaccharide, a secondary or higher order conformational structure, or a specific chemical group or combination of groups to form an active site). It is contemplated that the arrays formed by the process of this invention will be useful for screening chemical and molecular biological libraries for new therapeutic agents, for identifying ligands for known biological receptors and new receptors for known ligands, for identifying expressed genes, characterizing genetic polymorphisms, genotyping human populations for diagnostic and therapeutic purposes, and many other uses.

A. Array Light Detection

A detector is used for detecting the light resulting from light interaction in the array. Preferably, an array detector is used to measure individually the signal from each light source. At least one detector element is used to measure the signal from each light source, e.g., light source 12 in FIG. 1, in the array. However, more than one detector element may be used to over-sample the target chemicals, permitting the discrimination against non-uniformities. Over-sampling permits rapid signal detection with low power light sources. One example of an array detector is a solid-state semiconductor device, such as a charge-coupled device (CCD) array. Solid-state semi-conductor detector arrays can be cooled by a thermal electric cooler to reduce dark charge accumulation so as to improve the noise performance and the sensitivity of the analytical technique.

The excitation light from a light source impinges on the label (e.g., a fluorescent molecule bound to the analyte in the target chemical) and causes it to emit light as the light interaction signal. Only tiles with a target chemical, having a label, will emit the light interaction signal. The detected light interaction signals are synchronized with electronic excitation for light sources and processed, preferably by an electronic processing unit, such as a microprocessor or a computer. By analyzing the pattern of the light interaction in the array, the identity of the analytes in the sample can be determined.

Having different target chemicals bound on a surface on different individual light sources without intervening mechanical structures (such as lenses, prisms, beam-steering mechanisms) allows compact array apparatuses to be made. Further, the need for imaging optics to channel excitation light to the target chemicals from the light sources is obviated. Not requiring such optics is advantageous because intervening optics such as a lens may create aberration and distort the path of the excitation light. Furthermore, such optics are imperfect and surfaces of their optical elements inevitably cause some light scattering and result in increased noise.

B. Multiplexing

Instead of using an array detector to detect the light interaction, a single element optical detector may be used. To this end, either temporal multiplexing or frequency multiplexing can be done.

In temporal multiplexing, the light sources, e.g., light source 12, can be excited, i.e., activated, in a temporally multiplexed manner. In temporal multiplexing, the light sources ire activated individually and sequentially. The light interaction signals are detected by the same detector. Since the time of activation and the time of light interaction is known for each of the tiles, and they are different among the tiles, the identity of each of the tiles that emit light interaction signals is known. As a result, the light interaction pattern can be analyzed to obtain the desired information on the analytes in the sample.

In frequency multiplexing, the light sources in the array are excited simultaneously and a single light detector can be used to detect the light interaction signals. Each of the light sources is controlled such that the intensity of its excitation light varies regularly periodically, e.g., in sinusoidal form, square-wave form, saw-tooth form, and the like. The frequency of this light-intensity variation is different for each of the light sources. As a result, the frequency of the light-interaction signals will be different from light source to light source. By analyzing the frequencies of the light interaction signals when the light sources are activated, the identity of the tiles that result in light interaction, indicating the binding of target chemicals, can be determined. A spectrum analyzer can be connected to receive electrical signals from the light detector for the purpose of analyzing the spectrum of the light interaction signals detected by the light detector. The individual signals can be resolved and measured by the spectrum analyzer. The spectrum analysis can be done in an analog fashion by means of multiple modulators and demodulators, or by digital signals processing. In the latter case an analog to digital converter can be used to digitize the output of the light detector. The digitized data can be filtered by a digital filter in a computer, microprocessor, etc., with well known techniques, e.g., fast-Fourier transform.

Solid-state semiconductor devices are amenable to high-frequency modulation. Detection of the optical signals at a frequency, f, above the amplitude noise of the sources or the 1/f noise of the light detector will facilitate sensitive detection of target chemicals. The ability to employ the frequency multiplexing technique is advantageous in that analysis can be accomplished in a short time since all the light sources can be activated simultaneously. Furthermore, with the array of the present invention, there is no need to translate a light source or to steer a light beam to illumine the individual elements in the chemical array. Therefore, risk of mechanical failure is reduced.

Detecting light interaction with a suitable detector will result in a pattern of light interaction, in which certain locations in the pattern shows light interaction and certain locations do not. As previously stated, analyzing the pattern of light interaction in the array will provide information on the target chemicals, and therefore, of the analytes, bound to the tiles. The identity of a target chemical bound to a tile at any particular location in the array can be determined by detecting the location of the light interaction in the pattern and linking this with a tagged file of the array. The tagged file is a file of information wherein the identity and position of each binder chemical moiety in the array pertaining to the file is stored. There are various methods for linking this tagged file with the physical array. For example, the tagged file can be physically encoded on the array or its housing by means of a silicon chip, magnetic strip or bar code. Alternatively, the information identifying the array to a particular tagged file might be included on an array or its housing, with the actual file stored in the data analysis device or in a computer in communication with the device. The linking of the tagged file with the physical array would take place at the time of data analysis. Yet another way of linking would be to store the tagged file in a device such as a disk or card that could be inserted into the data analysis device by the array user at the time the array is used in the assay.

Although the illustrative embodiments of the apparatus of the present invention and the methods of making and using the apparatus have been described in detail, it is to be understood that the above-described embodiments can be modified by one skilled in the art, especially in sizes and shapes and combination of various described features without departing from the scope of the invention. For example, it is contemplated that an array can be made in which some, possibly most (e.g., more than 50%), but not all, of the tiles are made with the tiling process described.

What is claimed is:

1. An apparatus for analyzing target chemicals, comprising:
   an array of two or more light sources each having an emitting surface from which light is emitted from the light source; and
   two or more binder chemical moieties associated with the light sources at the emitting surfaces for binding target chemicals such that different target chemicals can be bound to the array, the light sources when activated will emit light to cause light interaction with the target chemicals to result in light pattern to indicate the presence or quantity of the target chemicals.

2. The apparatus according to claim 1 wherein the array is a tiled array and the light sources are solid-state light sources.

3. The apparatus according to claim 2 wherein 50% or more of the solid-state light sources are made by dividing wafers of solid-state light source material into smaller tiles of light sources.

4. The apparatus according to claim 2 wherein the light sources comprise one of light emitting diodes, vertical cavity surface emitting lasers, and edge-emitting diode lasers.

5. The apparatus according to claim 4 wherein on each light source at least one binder chemical moiety is present and not all the light sources have the same binder chemical moiety such that each of the target chemicals can associate with at least one of the light sources, wherein the light sources when activated emits light causing fluorescence in the target chemicals.

6. The apparatus according to claim 2 wherein the light sources comprise vertical cavity surface emitting lasers.

7. The apparatus according to claim 2 further comprising a detector for detecting light interaction.

8. The apparatus according to claim 2 further comprising a detector for detecting light interaction and comprising a controller for controlling the light sources such that the light sources can be energized in temporal sequence to result in temporal variation of the light interaction to detect the presence or quantity of the target chemicals.

9. The apparatus according to claim 2 further comprising a controller to control the light sources such that the light intensity of the light sources are varied periodically such that each binder chemical moiety is associated with a different frequency in light intensity variation to cause variation in light intensity in the light interaction and the apparatus further comprising a frequency analyzer to analyze the frequencies of the resulting light interaction to determine the presence or quantity of the target chemicals.

10. The apparatus according to claim 2 wherein the light sources are arranged such that they are activated in sequential groups and the apparatus further comprises a detector for detecting the pattern of light interaction in each group.

11. The apparatus according to claim 1 further comprising a fluid-handling system for introducing sample to the array.

12. A method of making an apparatus for analyzing target chemicals, comprising:
   arranging tiles of light sources into an array, the tiles of light sources having binder chemical moieties thereon for binding target chemicals such that each target chemical corresponds to at least one of the tiles in the array including binder chemical moiety suitable for binding the target chemical and such that different target chemicals can be bound to the array, the tiles of light sources when activated will emit light to cause light interaction with the target chemicals to result in light pattern to indicate the presence of the target chemicals.

13. The method according to claim 12 further comprising attaching one or more species of binder molecules having the binder chemical moieties on a surface on each of the light sources to obtain the tile.

14. The method according to claim 12 further comprising providing two or more wafers of solid-state light source material, attaching one or more binder chemical moieties on a surface on each of the wafers such that each target chemical has at least one of the wafers including binder chemical moiety suitable for binding the target chemical, and cleaving the wafers to obtain the tiles of light sources.

15. The method according to claim 14 wherein attaching the binder chemical moieties on a surface including attaching on the surface of a solid-state material selected from the group consisting of light emitting diode, edge-emitting diode laser, and vertical cavity surface emitting laser.

16. The method according to claim 14 further comprising electrically connecting the tiles of light sources to a controller capable of sequentially activating the tiles.

17. The method according to claim 14 further comprising electrically connecting the tiles of light sources to a controller capable of activating the tiles to vary in light intensity periodically such that each binder moiety is associated with a different frequency in light intensity variation to cause variation in light intensity in the light interaction.

18. The method according to claim 17 further comprising arranging a frequency analyzer to detect the light interaction and analyze the frequencies of the light interaction.

19. A method of making an apparatus for analyzing target chemicals, comprising:

(a) providing two or more wafers of solid-state vertical cavity surface emitting laser light source material, each having a planar light-emitting surface;

(b) attaching one or more species of binder molecules having binder chemical moieties on the planar light-emitting surface on each of the wafers for binding chemicals such that for each target chemical at least one wafer includes binder chemical moiety suitable for binding said each target chemical;

(c) cleaving the wafers along lines two-dimensionally on the planar surface to obtain tiles of light sources such that each tile has one or more straight edges; and (d) arranging a number of the tiles of light sources into an array such that each target chemical corresponds to at least one of the tiles in the array including binder chemical moiety suitable for binding the target chemical and such that different target chemicals can be bound to the array, and such that each tile when activated will emit light to cause light interaction with target chemical bound to the binder chemical moiety on the tile to result in light pattern to indicate the presence or quantity of the target chemical.

20. A method for analyzing target chemicals in a sample, comprising:

(a) providing an array of two or more light sources each having an emitting surface from which light is emitted from the light source and two or more binder chemical moieties associated with the light sources at the emitting surfaces for binding target chemicals such that different target chemicals can be bound to the array;

(b) washing the sample over the array to bind target chemicals in the sample to the light sources and rinsing to remove unbound portion of the sample;

(c) emitting light from the light sources to cause light interaction by target chemicals bound in the array, the light interaction resulting in a pattern of light; and (d) analyzing the pattern of light to determining the presence or quantity of target chemicals in the sample.

* * * * *